United States Patent

Kawamatsu et al.

[11] Patent Number: 4,461,902
[45] Date of Patent: Jul. 24, 1984

[54] THIAZOLIDINE DERIVATIVES AND PRODUCTION THEREOF

[75] Inventors: Yutaka Kawamatsu, Kyoto; Takeshi Fujita, Takarazuka, both of Japan

[73] Assignee: Takeda Chemical Industries, Ltd., Osaka, Japan

[21] Appl. No.: 454,356

[22] Filed: Dec. 29, 1982

[30] Foreign Application Priority Data

Jan. 7, 1982 [JP] Japan ................................. 57-1653

[51] Int. Cl.³ ................. C07D 277/34; A61K 31/425
[52] U.S. Cl. ..................................... 548/183; 424/270
[58] Field of Search ......................................... 548/183

[56] References Cited

U.S. PATENT DOCUMENTS 3,825,587  7/1974  Diamond ..................... 260/501.16
4,287,200  9/1981  Kawamatsu ..................... 424/270
4,376,777  3/1983  Kawamatsu et al. .............. 424/270

Primary Examiner—Robert Gerstl
Attorney, Agent, or Firm—Wenderoth, Lind & Ponack

[57] ABSTRACT

A thiazolidine derivative of the general formula,

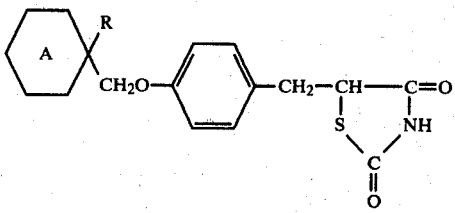

wherein 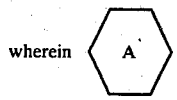

is a cyclohexane ring having an oxo or hydroxyl group as a substituent on any of the methylene groups constituting the ring and R is a hydrogen atom or a lower alkyl group having 1 to 4 carbon atoms, is a novel compound and is useful as, for example, remedies for diabetes, hyperlipemia and so on of mammals including human beings.

9 Claims, No Drawings

THIAZOLIDINE DERIVATIVES AND PRODUCTION THEREOF

This invention relates to novel thiazolidine derivatives having blood lipid- and sugar-lowering activity and a method of producing the same. More particularly, the present invention relates to:

(1) Thiazolidine derivatives of the general formula:

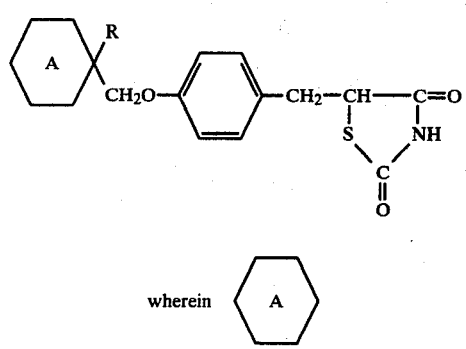

is a cyclohexane ring having an oxo or hydroxyl group as a substituent on any of the methylene groups constituting the ring and R is a hydrogen atom or a lower alkyl group having 1 to 4 carbon atoms;

(2) A method of producing thiazolidine derivatives of general formula (I), which comprises reacting a compound of the general formula:

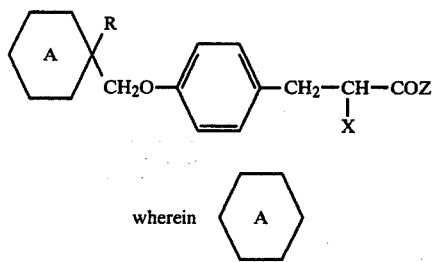

and R are as defined above, X is a halogen atom and Z is a hydroxyl or alkoxy group, with thiourea and hydrolyzing the resulting product.

In the above general formulas (I) and (II), the lower alkyl group having 1 to 4 carbon atoms represented by R includes straight or branched alkyls such as methyl, ethyl, n-propyl, iso-propyl, n-butyl and iso-butyl. The halogen atom represented by X includes, for example, chlorine and bromine, and the alkoxy group represented by Z includes alkoxy groups having 1 to 10 carbon atoms (such as methoxy, ethoxy, n-propoxy, n-butoxy, iso-butoxy, tert-butoxy and n-pentyloxy), though alkoxy having 1 to 4 carbon atoms is preferable.

The compounds of the present invention as represented by general formula (I) can be converted in a conventional manner into corresponding salts with various cations such as alkali metals (e.g. sodium, potassium), alkaline earth metals (e.g. calcium) and ammonium.

The thiazolidine derivatives (I) of the present invention have hypolipidemic and hypoglycemic activity in spontaneously diabetic KKA$^y$ strain mice and is expected to be of value in the treatment of hyperlipemia, diabetes and their complications in mammals including human beings. The thiazolidine derivatives (I) have low toxicity. For instance, 5-[4-(1-methyl-2-oxocyclohexylmethoxy)benzyl]thiazolidine-2,4-dione, 5-[4-(1-methyl-3-oxocyclohexylmethoxy)benzyl]thiazolidine-2,4-dione, 5-[4-(1-methyl-4-oxocyclohexylmethoxy)benzyl]thiazolidine-2,4-dione and 5-[4-(4-hydroxy-1-methylcyclohexylmethoxy)benzyl]thiazolidine-2,4-dione all have an $LD_{50}$ value of 5 g/kg or more in mice. They can be administered orally in the form of tablets, capsules, powders and granules, for instance, as well as parenterally in the form of injectable solutions, suppositories, pellets, etc. In treating hyperlipemia, they can be administered orally or parenterally, generally in daily doses of 50 mg to 1 g, preferably 100 mg to 500 mg, per adult human and in treating diabetes, they can be used orally or parenterally, generally in daily doses of 10 mg to 1 g, preferably 100 mg to 500 mg, per adult human.

The thiazolidine derivatives (I) of the present invention can be produced, for example, in the following manner. Thus, they can be produced by reacting a compound of general formula (II) with thiourea to give a compound (III) and hydrolyzing the resulting compound of the general formula

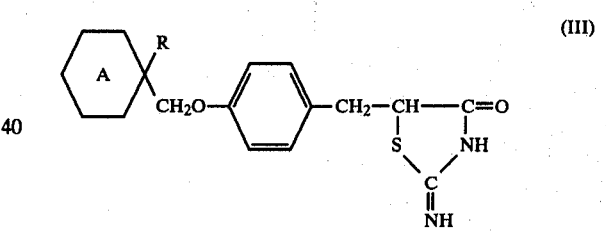

wherein the symbols are as defined above. For compound (III), presumably there are tautomers as represented by the formulas shown below. For convenience sake, however, they are referred to simply as "compound (III)".

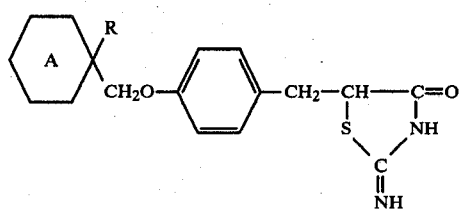 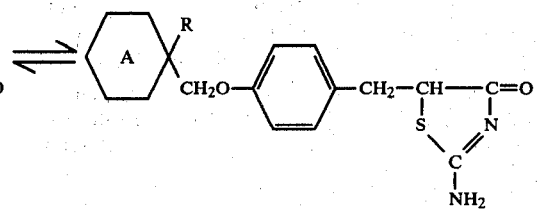

wherein the symbols are as defined above.

The reaction of compound (II) with thiourea is generally carried out in a solvent. Usable solvents are, for example, alcohols such as methanol, ethanol, propanol, butanol and ethylene glycol monomethyl ether, ethers such as tetrahydrofuran and dioxane, and further acetone, dimethyl sulfoxide, sulfolane and dimethylformamide. Although the molar ratio between compound (II) and thiourea to come into contact with each other is not critical, thioures is advisably used in an equimolar or slightly excess amount as compared with compound (II). Preferably, 1-2 moles of thiourea is used per mole of compound (II). The reaction conditions, such as reaction temperature and reaction time, are to be selected depending on the starting material, solvent and other factors. Generally, the reaction is carried out at the boiling point of the solvent or 50°-130° C., preferably at the boiling point of the solvent or 70°-130° C., for one to ten-odd hours. In this manner, compounds (III) can be obtained. These compounds (III) may be isolated prior to the following hydrolysis step or may be subjected to the next hydrolysis step without isolation thereof. As the starting materials for the above reaction, there may also be used those compounds (II) that have on the cyclohexane ring an oxo or hydroxyl group protected with a protective group easily eliminable with an acid. Examples of the oxo-protecting group are ketals such as ethylene ketal and ethylene dithioketal, and examples of the hydroxyl-protecting group are acyl groups such as acetyl, alkoxyalkyl groups such as methoxymethyl and 2-tetrahydropyranyl. The use of such compound (II) having a protected hydroxyl or oxo group on the cyclohexane ring as the starting material leads to compound (III) having the correspondingly protected hydroxyl or oxo group, which compound (III) as it is may be subjected to the next hydrolysis step without elimination of the protective group.

The hydrolysis is carried out in an appropriate solvent (e.g. alcohols such as methanol, ethanol, propanol, butanol and ethylene glycol monomethyl ether, ethers such as tetrahydrofuran and dioxane, and further acetone, dimethyl sulfoxide, sulfolane and dimethylformamide) in the presence of water and a mineral acid. The acid is added generally in an amount of 0.1 to 10 moles, preferably 0.2 to 3 moles, per mole of compound (III) and water is added generally in an amount of 2 to 300 moles, preferably 10 to 200 moles, per mole of compound (III). The reaction is generally carried out for several to ten-odd hours. The use of a compound (III) having a protected hydroxyl or oxo group on the cyclohexane ring also leads to compound (I) since simultaneously the protective group is eliminated by the reaction of the acid.

In cases where the cyclohexane ring of the thus-obtained thiazolidine derivatives (I) has a hydroxyl group, such compounds (I) may further be converted to those compounds (I) which have an oxo group as the substituent on the cyclohexane ring by oxidation, while those compounds (I) which have an oxo group on the cyclohexane ring may be converted to the corresponding hydroxyl group-containing compounds (I) by reduction. Preferable oxidizing agents in the case of oxidation are chromium trioxide species (e.g. Jones' reagent, chromium trioxide-pyridine) and preferable reducing agents in the case of reduction are sodium borohydride and aluminum isopropoxide-isopropanol. However, other reagents may also be used if the conditions are appropriately selected. In cases where the cyclohexane ring has a hydroxyl group, said hydroxyl group may have either the cis or the trans configuration with respect to the group

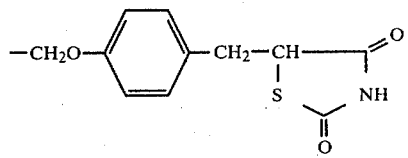

and it should be noted that both the isomers are included among the compounds of the present invention.

The thiazolidine derivatives (I) can be isolated and purified by conventional separation/purification methods, for example, concentration, concentration under reduced pressure, solvent extraction, crystallization, recrystallization, phase transfer and chromatography.

The α-halocarboxylic acids (II) which are used as the starting materials in the production of the compounds (I) of the present invention are synthesized, for instance, by the process illustrated below. The corresponding anilines (VII) are diazotized and the diazonium salts are subjected to Meerwein arylation to give compounds (II).

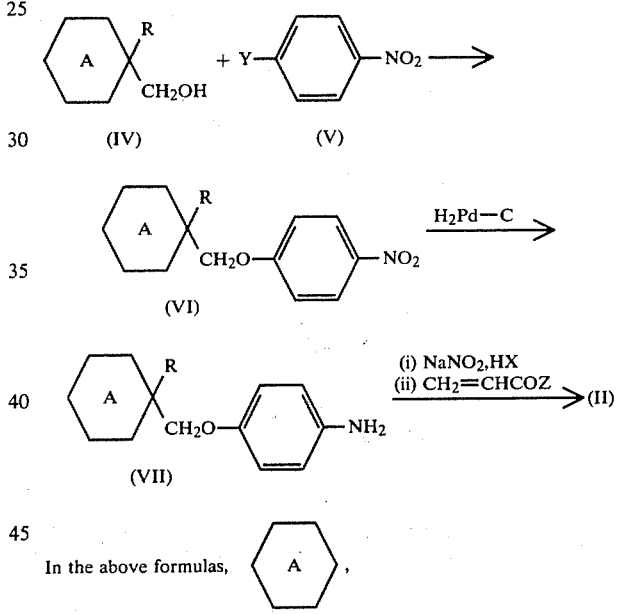

In the above formulas,

R, X and Z are as defined previously, and Y is a halogen atom.

In the above general formula (V), the halogen atom represented by Y includes fluorine and chlorine. In compounds (IV), (VI) and (VII), the hydroxyl or oxo group on the cyclohexane ring is a hydroxyl or oxo group unprotected or protected with a protective group easily eliminable upon treatment with an acid. Such protective group includes, for the hydroxyl group protection, 2-tetrahydropyranyl, methoxymethyl, acetyl and so on, among which 2-tetrahydropyranyl is preferred, and for the oxo group protection, various alkylene ketals and alkylene thioketals, among which ethylene ketal is preferred.

The reaction between the cyclohexanemethanol derivative of general formula (IV) and the 4-halonitrobenzen (V) is generally carried out in a solvent, such as dimethyl sulfoxide, N,N-formamide, N,N-dimethylacetamide, at room temperature to 100° C. in the presence of a base, such as sodium hydride, potassium hydroxide, sodium hydroxide or potassium carbonate. For instance, (IV) and (V) are reacted in equimolar amounts in dimethyl sulfoxide at 50° C. in the presence of sodium hydide to give a nitro compound (VI). The protective group of the hydroxyl or oxo group on the cyclohexane ring may be eliminated from the nitro compound (VI) under the respective elimination conditions. The thus-obtained nitro compound (VI) is reduced to an aniline (VII). The reduction includes catalytic reduction, use of zinc-acetic acid and use of iron-acetic acid, for instance, among which catalytic reduction is preferred. The catalytic reduction is carried out in a solvent, such as an alcohol, a benzene-series solvent (e.g. benzene, toluene), an ether (e.g. tetrahydrofuran, isopropyl ether, dioxane) or ethyl acetate, at 0° C. to 100° C. and 1 to 100 atmospheres, preferably at room temperature and 1 atmosphere, using palladium-on-carbon, platinum oxide or the like as the catalyst. Anilines (VII), which are mostly oils, are submitted to the next Meerwein arylation step without purification. The Meerwein arylation is generally carried out, after diazotization in a solvent such as an alcohol (e.g. methanol, ethanol) and acetone, preferably in methanol or acetone, under usual diazotization conditions, by adding acrylic acid or the like and a catalytic amount of a cuprous salt in the presence of 2-10 equivalents, preferably 2-3 equivalents, of an acid. Acrylic acid or the like is used in an amount of 3-10 equivalents, preferably 6-7 equivalents. The cuprous salt includes cuprous chloride, cuprous oxide and so forth, among which cuprous oxide is preferred. The reaction is generally carried out at room temperature to 50° C., preferably 30°-40° C. Generally, the anilines having a protected hydroxyl or oxo group on the cyclohexane ring are partly deprived of the protective group in the course of this Meerwein arylation reaction. If necessary, complete protective group elimination can be attained by additional acid treatment.

The above-mentioned cyclohexanemethanol derivatives (IV) can be synthesized by protecting the hydroxyl or oxo group of a hydroxy ester or keto ester obtainable, for example, by the method (i), (ii), (iii) or (iv) shown below, and then reducing the resulting compound with a reducing agent such as lithium aluminum hydride.

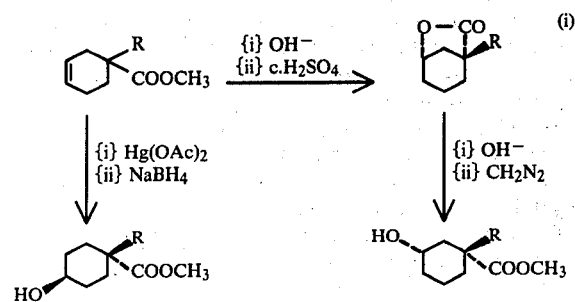

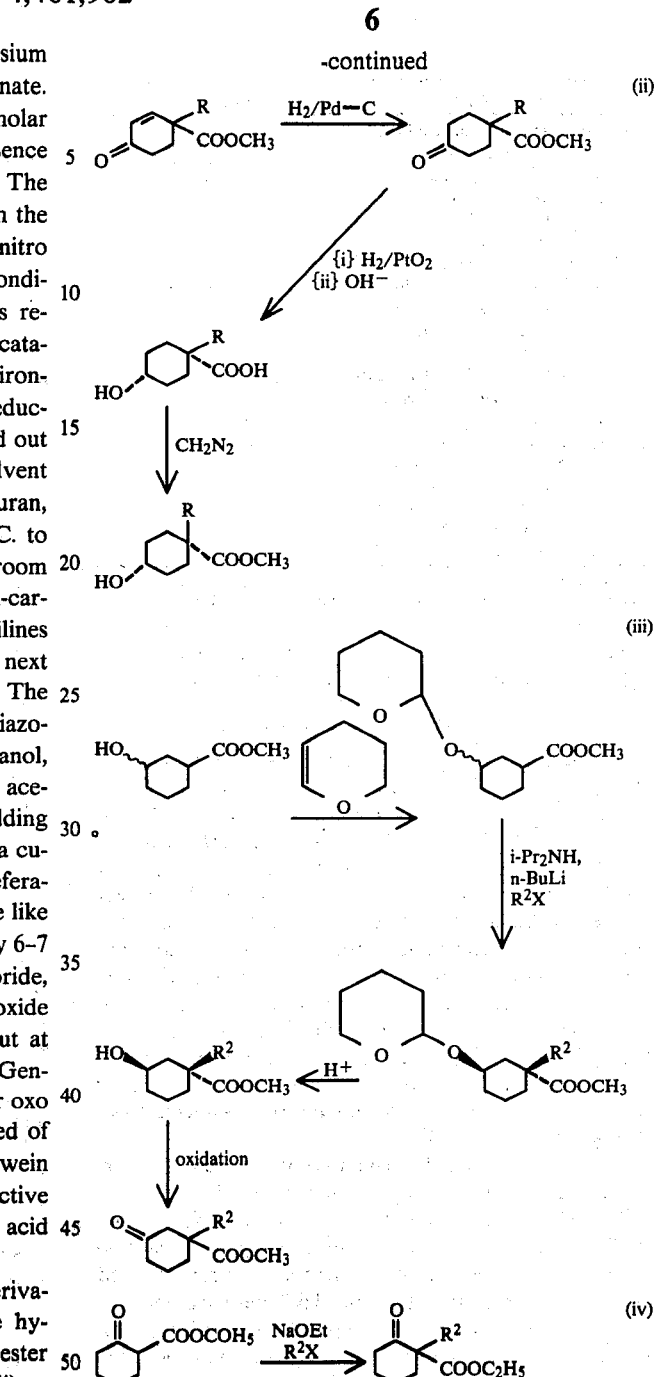

The compounds of the present invention have excellent hypoglycemic activity as evidenced by the following test.

Hypoglycemic activity in mice

KKA$^y$ mice (female, 10 weeks of age, 5 mice/group) received ad libitum powder diet CE2 (CLEA JAPAN) containing 0.02% of the compounds indicated below in the table mixed therewith for 4 days. Water was available ad libitum throughout the period. Blood sample were taken from the orbital vein and assayed for blood sugar by the glucose oxidase method. The hypoglycemic activity of the test compound 1 was regarded as 100 and the activity of each of the remaining test compounds was expressed in terms of relatve potency and indicated in the table below.

| Test compounds | Hypoglycemic activity |
| --- | --- |
| {1} 5-[4-(1-methylcyclohexylmethoxy-benzyl]thiazolidine-2,4-dione | 100 |
| {2} 5-[4-(t-4-hydroxy-1-methyl-r-cyclohexylmethoxy)benzyl]-thiazolidine-2,4-dione | 118 |
| {3} 5-[4-(1-methyl-2-oxocyclohexylmethoxy)-benzyl]thiazolidine-2,4-dione | 179 |
| {4} 5-[4-(2-hydroxy-1-methylcyclo-hexylmethoxy)benzyl]thiazolidine-2,4-dione* | 114 |
| {5} 5-[4-(3-hydroxy-1-methylcyclo-hexylmethoxy)benzyl]thiazolidine-2,4-dione* | 148 |
| {6} 5-[4-(t-3-hydroxy-1-methyl-r-1-cyclohexylmethoxy)benzyl]-thiazolidine-2,4-dione | 369 |
| {7} 5-[4-(c-3-hydroxy-1-methyl-r-1-cyclohexylmethoxy)benzyl]-thiazolidine-2,4-dione | 125 |

*A mixture of two (cis and trans) isomers having different configurations with respect to the hydroxyl group (synthesized by the procedure of Example 2)

The following reference examples and embodiment examples illustrate the present invention in more detail.

REFERENCE EXAMPLE 1

A solution of 1-methyl-3-cyclohexenecarboxylic acid (47 g) in chloroform (200 ml) was cooled to −5° C. Then, a mixture of conc. $H_2SO_4$ (100 ml) and chloroform (100 ml) was added. After stirring at 0° C. for 15 minutes, the mixture was poured onto ice (500 g) and extracted with chloroform. The chloroform layer was washed in sequence with water, saturated aqueous sodium hydrogen carbonate solution and water, and dried ($MgSO_4$), and the chloroform was distilled off. The residual oily substance was subjected to column chromatography using silica gel (500 g) and eluted with ether-hexane (1:3 v/v). From the first eluate fractions, crystals of 1-methylcyclohexane-1,3-carbolactone (28.0 g, 59.6% yield) were recovered and recrystallized from hexane. m.p. 37°–38° C.

The thus-obtained 1-methylcyclohexane-1,3-carbolactone (9.8 g) was dissolved in methanol (70 ml), and 2N KOH (70 ml) was added. The mixture was heated under reflux for 3 hours. After cooling, the reaction mixture was concentrated to about ½ under reduced pressure, made acid with conc. HCl with ice-cooling, and extracted with ethyl acetate. After washing with water and drying ($MgSO_4$), the ethyl acetate was distilled off. Crystals of c-3-hydroxy-1-methyl-r-1-cyclohexanecarboxylic acid (9.0 g, 81.8% yield) were thus obtained and recrystallized from ethyl acetate-hexane. m.p. 131°–132° C.

c-3-Hydroxy-1-methyl-r-1-cyclohexanecarboxylic acid (8.8 g) was suspended in ether (100 ml), and thereto was added a solution of diazomethane in ether (prepared from 15 g of nitrosomethylurea) with ice-cooling. The mixture was stirred at room temperature for 30 minutes, and then acetic acid (6 ml) was added. The mixture was washed in sequence with water, saturated aqueous sodium hydrogen carbonate solution and water, and dried ($MgSO_4$), and the ether was distilled off to give methyl c-3-hydroxy-1-methyl-r-1-cyclohexanecarboxylate as an oil (9.5 g, 99.0% yield).

IR $\nu_{max}^{Neat}$ cm$^{-1}$: 3400, 1730

NMR δ ppm in $CDCl_3$: 1.18 (3H, s), 1.2–2.2 (8H, m), 2.70 (1H, broad), 3.68 (3H, s), 3.85 (1H, m)

REFERENCE EXAMPLE 2

Mercuric acetate (100 g) was dissolved in tetrahydrofuran (300 ml)-water (300 ml), and methyl 1-methyl-3-cyclohexanecarboxylate [J. Am. Chem. Soc., 71, 3248 (1948)] (48.4 g) was added thereto. The mixture was stirred at room temperature for 30 minutes, and 3N NaOH (300 ml) was then added. Thereafter, a solution of sodium borohydride (8.0 g) in 3N NaOH (300 ml) was added dropwise at a temperature of 20° C. or below, the precipitated mercury was separated, and the solution was extracted with ether. The extract was washed with water and dried ($MgSO_4$), the solvent was distilled off, and the residue was distilled under reduced pressure to give methyl t-4-hydroxy-1-methyl-r-1-cyclohexanecarboxylate (20.0 g, 37.0%, b.p. 90°–93° C./0.5 mmHg).

IR $\nu_{max}^{Neat}$ cm$^{-1}$: 3400, 1725

NMR δ ppm in $CDCl_3$: 1.20(3H, s), 1.4–2.0(8H, m), 3.68(3H, s), 3.6–3.9(1H, broad)

The aqueous layer remaining after the above-mentioned ether extraction was made acid with conc. HCl and then extracted with ethyl acetate. The extract was washed with water and dried ($MgSO_4$), and the ethyl acetate was distilled off. There were obtained crystals (11.7 g, 23.5%) of t-4-hydroxy-1-methyl-r-1-cyclohexane carboxylic acid. They were recrystallized from ethyl acetate-hexane. m.p. 138°–139° C. The thus-obtained t-4-hydroxy-1-methyl-r-1-cyclohexanecarboxylic acid was converted to the same methyl ester as that obtained previously by conventional esterification method (with diazomethane or sulfuric acid-methanol).

REFERENCE EXAMPLE 3

Methyl 1-methyl-4-oxo-2-cyclohexenecarboxylate [J. Am. Chem. Soc., 101, 6996 (1979)] (100 g) was dissolved in ethyl acetate (600 ml), 10% Pd-C (5 g) was added, and catalytic reduction was carried out at room temperature and 1 atomosphere. About 14 liters of hydrogen was absorbed in about 2 hours. The catalyst was filtered off, and the filtrate was concentrated and distilled under reduced pressure to give methyl 1-methyl-4-oxocyclohexanecarboxylate (96.5 g, 95.4%, b.p. 82°–84° C./0.5 mmHg).

IR $\nu_{max}^{Neat}$ cm$^{-1}$: 1730, 1715

NMR δ ppm in $CDCl_3$: 1.32(3H, s), 1.5–2.7(8H, m), 3.80(3H, s)

REFERENCE EXAMPLE 4

Methyl 1-methyl-4-oxocyclohexanecarboxylate (5.0 g) was dissolved in methanol (50 ml), $PtO_2$ (0.6 g) was added, and catalytic reduction was carried out at room temperature and 1 atmosphere. After adsorption of about 0.7 liter of hydrogen, the catalyst was filtered off and 4N KOH (20 ml) was added. The mixture was stirred at 60° C. for an hour, concentrated, made acid with 6N HCl and extracted with ethyl acetate. The extract was washed with water and dried ($MgSO_4$), and the solvent was distilled off. The crystalline residue was collected by filtration and recrystallized from ethyl acetate to give c-4-hydroxy-1-methyl-r-1-cyclohexanecarboxylic acid (2.35 g, 50.5%, m.p. 164°–165° C.).

The thus-obtained c-4-hydroxy-1-methyl-r-1-cyclohexanecarboxylic acid was treated with a solution of diazomethane in ether in a conventional manner to give methyl c-4-hydroxy-1-methyl-r-1-cyclohexanecarboxylate in quantitative yield.

IR $\nu_{max}^{Neat}$ cm$^{-1}$: 3380, 1725

NMR δ ppm in CDCl$_3$: 1.15(3H, s), 1.2–2.4(8H, m), 2.62(1H, broad), 3.55(1H, broad), 3.67(3H, s)

REFERENCE EXAMPLE 5

To a solution of methyl 3-hydroxycyclohexanecarboxylate [J. Am. Chem. Soc., 70, 1898 (1948)] (61 g) in ether (500 ml), 2,3-dihydropyran (49 g) and p-toluenesulfonic acid monohydrate (1 g) were added. The mixture was stirred at room temperature for 6 hours and washed with water and dried (MgSO$_4$). The ether was distilled off, and the oily residue was distilled under reduced pressure to give methyl 3-(2-tetrahydropyranyloxy)cyclohexanecarboxylate (61.5 g, 60.2%, b.p. 120°–123° C./0.3 mmHg).

Separately, to a solution of diisopropylamine (37.6 g) in dry tetrahydrofuran (0.8 liter), a solution of n-butyllithium in hexane (1.62N, 229 ml) was added dropwise at −65° C. under nitrogen. The mixture was stirred at the same temperature for 30 minutes. To this solution was added dropwise at −60° C. or below a solution of the above-mentioned methyl 3-(2-tetrahydropyranyloxy)cyclohexanecarboxylate (60.0 g) in dry tetrahydrofuran (200 ml). After the resulting mixture was stirred at −70° C. for one hour, methyl iodide (52.7 g) was added dropwise at −60° C. or below. The mixture was stirred at −70° C. for 2 hours, then the cooling bath was removed, and the mixture was stirred until it reached to room temperature. The reaction mixture was then poured into ice-water and extracted with ether. The organic layer was washed with water and dried (MgSO$_4$). The solvent was distilled off under reduced pressure, and the residue was distilled under reduced pressure to give methyl 1-methyl-t-3-(2-tetrahydropyranyloxy)-r-1-cyclohexanecarboxylate (61.0 g, 95.9%, b.p. 120°–125° C./0.3 mmHg).

IR $\nu_{max}^{Neat}$cm$^{-1}$: 1730

NMR δ ppm in CDCl$_3$: 1.18(3H, s), 1.1–2.1(14H, m), 3.65(3H, s), 3.3–4.1(3H, m), 4.70(1H, broad)

To a solution of the thus-obtained methyl 1-methyl-t-3-2-(tetrahydropyranyloxy)-r-1-cyclohexanecarboxylate (60.0 g) in tetrahydrofuran (400 ml), 2N HCl (400 ml) was added, and the mixture was stirred at room temperature for 3 hours and then allowed to stand overnight. Water was then added and extraction was performed with ether. The organic layer was washed in sequence with water, saturated aqueous sodium hydrogen carbonate and water, and dried (MgSO$_4$), and the solvent was distilled off. The oily residue was distilled under reduced pressure to give methyl t-3-hydroxy-1-methyl-r-1-cyclohexanecarboxylate (36.8 g, 91.3%, b.p. 110°–113° C./0.5 mmHg).

IR $\nu_{max}^{Neat}$cm$^{-1}$: 3370, 1730

NMR δ ppm in CDCl$_3$: 1.18(3H, s), 1.1–2.2(8H, m), 3.40(1H, broad), 3.65(3H, s)

REFERENCE EXAMPLE 6

To a solution of methyl t-3-hydroxy-1-methyl-r-1-cyclohexanecarboxylate (22.0 g) in acetone (200 ml), Jones' reagent (40 ml) was added dropwise with ice-cooling. After the mixture was stirred with ice-cooling for 30 minutes, methanol (10 ml) was added, and stirring was continued for further 5 minutes. The mixture was concentrated under reduced pressure, diluted with water, and extracted with ether. The ether layer was washed with water and dried (MgSO$_4$). The other was distilled off, and the oily residue was distilled under reduced pressure to give methyl 1-methyl-3-oxocyclohexanecarboxylate (18.5 g, 85.3%, b.p. 87°–90° C./0.3 mmHg).

IR $\nu_{max}^{Neat}$cm$^{-1}$: 1725(broad)

NMR δ ppm in CDCl$_3$: 1.27(3H, s), 1.6–2.9(8H, m), 3.71(3H, s)

REFERENCE EXAMPLE 7

Methyl 1-methyl-4-oxocyclohexanecarboxylate (30 g) was dissolved in benzene (300 ml). Ethylene glycol (30 ml) and p-toluenesulfonic acid monohydrate (1 g) were added, and the mixture was refluxed for 4 hours. The water which formed during the heating was removed by using a water trap. After cooling, the mixture was washed with water and dryed (MgSO$_4$). The solvent was distilled off to give methyl 4,4-ethylenedioxy-1-methylcyclohexanecarboxylate as an oil (37.8 g, 100%).

IR $\nu_{max}^{Neat}$cm$^{-1}$: 1720

NMR δ ppm in CDCl$_3$: 1.20(3H, s), 1.4–2.4(8H, m), 3.70(3H, s), 3.95(4H, s)

The thus-obtained methyl 4,4-ethylenedioxy-1-methylcyclohexanecarboxylate (37.8 g) was dissolved in ether (100 ml), and the solution was added dropwise to a refluxing suspension of LiAlH$_4$ (6.7 g) in ether (400 ml). After the addition, the mixture was stirred at room temperature for an hour and then cooled with ice. Ethyl acetate (20 ml) and then water (35 ml) were added dropwise cautiously thereto. The solid precipitate was filtered off, and the filtrate was distilled under reduced pressure to give 4,4-ethylenedioxy-1-methylcyclohexanemethanol (29.5 g, 89.9% yield, b.p. 120°–125° C./0.5 mmHg, m.p. 42°–43° C.).

REFERENCE EXAMPLE 8

By a similar manner to Reference Example 7, the following compounds were prepared.

2,2-Ethylenedioxy-1-methylcyclohexanemethanol

Yield: 79.6% {yield from ethyl 1-methyl-2-oxocyclohexanecarboxylate [J. Org. Chem, 21, 612 (1956)]}
b.p. 105°–108° C./1 mmHg
IR $\nu_{max}^{Neat}$cm$^{-1}$: 3400
NMR δ ppm in CDCl$_3$: 1.0(3H, s), 1.6(8H, broad), 3.15(1H d, J=6), 3.65(2H, d, J=6), 4.07(4H, s)

3,3-Ethylenedioxy-1-methylcyclohexanemethanol

Yield: 77.9% (yield from methyl 1-methyl-3-oxocyclohexanecarboxylate)
IR $_{max}^{Neat}$cm$^{-1}$: 3420
NMR Δ ppm in CDCl$_3$: 0.93(3H, s), 1.3–2.0(8H, m), 2.83(1H, broad), 3.33(2H, broad), 3.87(4H, s)

4,4-Ethylenedioxycyclohexanemethanol

Yield: 89.5% {yield from ethyl 4-oxocyclohexanecarboxylate [Helv. 27, 793 (1944)]}
IR $\nu_{max}^{Neat}$cm$^{-1}$: 3400
NMR δ ppm in CDCl$_3$: 1.0–2.0(9H, m), 2.72(1H, broad), 3.50(2H, broad), 3.93(4H, s)

REFERENCE EXAMPLE 9

To a solution of methyl c-4-hydroxy-1-methyl-r-1-cyclohexanecarboxylate (15.5 g) in ether (150 ml), 2,3-dihydropyran (9.1 g) and p-toluenesulfonic acid monohydrate (0.1 g) were added, and the mixture was stirred at room temperature for an hour and then allowed to stand overnight. The mixture was washed with water and dried (MgSO$_4$), and the solvent was distilled off under reduced pressure. The thus-obtained oil was reduced with lithium aluminum hydride (3.8 g) in the same manner as in Reference Example 7 to give 1-methyl-c-4-(2-tetrahydropyranyloxy)-r-1-cyclohexanemethanol as a crude oil. The oil was subjected to column chromatography using silica gel (200 g). Elution with ether-hexane (2:3, v/v) gave 15.7 g (76.6%) of an oil.

IR $\nu_{max}^{Neat}$ cm$^{-1}$: 3400

NMR $\delta$ ppm in CDCl$_3$: 0.93(3H, s), 1.2–2.0(14H, broad), 2.30(1H, broad) 3.4–4.0(5H, m), 4.78(1H, broad)

REFERENCE EXAMPLE 10

By a similar manner to Reference Example 9, the following compounds were prepared.

1-Methyl-t-4-(2-tetrahydropyranyloxy)-r-1-cyclohexanemethanol

Yield: 63.4%

IR $\nu_{max}^{Neat}$ cm$^{-1}$: 3420

NMR $\delta$ ppm in CDCl$_3$: 0.92(3H, s), 1.1–2.0(15H, m), 3.30(2H, broad s), 3.4–3.7(2H, m), 3.75–4.05(1H, m), 4.71(1H, broad)

1-Methyl-c-3-(2-tetrahydropyranyloxy)-r-1-cyclohexanemethanol

Yield: 71.0%

IR $\nu_{max}^{Neat}$ cm$^{-1}$: 3430

NMR $\delta$ ppm in CDCl$_3$: 0.90(3H, s), 1.1–2.0(14H, m), 2.07(1H, broad), 3.30(2H, s), 3.3–3.6(1H, m), 3.6–4.1(2H, m) 4.70(1H, broad)

1-Methyl-t-3-(2-tetrahydropyranyloxy)-r-1-cyclohexanemethanol

Yield: 58.8%

IR $\nu_{max}^{Neat}$ cm$^{-1}$: 3400

NMR $\delta$ ppm in CDCl$_3$: 0.96(3H, s), 1.1–2.0(14H, m), 3.2–4.1(6H, m), 4.70 (1H, broad)

REFERENCE EXAMPLE 11

To a solution of 1-methyl-c-4-(2-tetrahydropyranyloxy)-r-1-cyclohexanemethanol (15.5 g) and p-fluoronitrobenzene (9.6 g) in dimethyl sulfoxide (150 ml), 60% sodium hydride (3.3 g) was added, and the mixture was stirred at 45° C. for 2 hours. The reaction mixture was poured into ice water and extracted with ether. The ether layer was washed with water and dried (MgSO$_4$), and the ether was distilled off. The oily residue was dissolved in methanol (200 ml) and 2N HCl (60 ml) was added thereto. The mixture was stirred at room temperature for an hour, then poured into water and extracted with ether. The ether layer was washed with water and dried (MgSO$_4$). The ether was distilled off, and the residue was treated with ether-hexane to give 4-(c-4-hydroxy-1-methyl-r-1-cyclohexylmethoxy)nitrobenzene (13.5 g, 75.0%). This was recrystallized from ether-hexane. m.p. 99°–100° C.

REFERENCE EXAMPLE 12

To a solution of 3,3-ethylenedioxy-1-methylcyclohexanemethnol (9.5 g) and p-chloronitrobenzene (8.0 g) in dimethyl sulfoxide (100 ml), 60% sodium hydride (2.2 g) was added. The mixture was stirred at 50° C. for 2 hours, then poured into ice water and extracted with ether. The ether layer was washed with water and dried (MgSO$_4$), and the ether was distilled off. The oily residue was subjected to column chromatography using silica gel (200 g). Elution with ether-hexane (1:10, v/v) gave 4-(3-ethylenedioxy-1-methylcyclohexylmethoxy)nitrobenzene (9.3 g, 59.2%) as an oil.

IR $\nu_{max}^{Neat}$ cm$^{-1}$: 1585, 1335

NMR $\delta$ ppm in CDCl$_3$: 1.12(3H, s), 1.2 1.8(8H, m), 3.92(3H, s), 7.03(2H, d, J=9), 8.26(2H, d, J=9)

REFERENCE EXAMPLE 13

Following the procedure of the above Reference Example 11 or 12, the following compounds were synthesized.

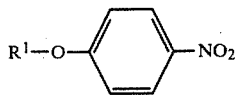

| R$^1$ | m.p. (°C.) | recrystallization solvent | Yield | Analogous Reference Example |
|---|---|---|---|---|
| ![structure with dioxolane, CH3, CH2−] | 92–93 | methanol | 82.3 | 12 |
| ![structure with dioxolane, CH3, CH2−] | 73–74 | methanol | 77.4 | 12 |
| ![structure with HO, CH3, CH2−] | 120–121 | ether-hexane | 58.9 | 11 |

-continued $$R^1-O-\underset{}{\underset{}{\bigcirc}}-NO_2$$

| $R^1$ | m.p. (°C.) | recrystallization solvent | Yield | Analogous Reference Example |
|---|---|---|---|---|
| HO—[cyclohexyl(CH₃)(CH₂—)] | 114–115 | ethyl acetate-hexane | 68.8 | 11 |
| [tetrahydropyranyl-O-cyclohexyl(CH₃)(CH₂—)] | 95–96 | methanol | 60.0 | 12 |
| [dioxolane-cyclohexyl-CH₂—] | 125–126 | methanol | 76.9 | 12 |

REFERENCE EXAMPLE 14

4-[t-4-(2-Tetrahydropyranyloxy)-1-methyl-r-1-cyclohexylmethoxy]nitrobenzene (12.5 g) was dissolved in methanol (150 ml), 10% Pd-C (2 g) was added, and catalytic reduction was carried out at room temperature and 1 atmosphere. About 2.5 liters of hydrogen was absorbed in an hour. The catalyst was filtered off, and the filtrate was concentrated under reduced pressure. The oily residue was dissolved in acetone (200 ml) and the solution was cooled to 0° C. conc. HCl (8.9 ml) was added and then a solution of NaNO₂ (2.7 g) in water (10 ml) was added dropwise at 5° C. or below. After the mixture was stirred at 5° C. for 15 minutes, methyl acrylate (18.5 g) was added, and the resulting mixture was warmed to 35° C. Cuprous oxide powder (0.5 g) was added portionwise with vigorous stirring, whereupon violent nitrogen gas evolution occurred with evolution of heat. Stirring was continued until the mixture returned to room temperature. The mixture was then allowed to stand overnight and concentrated under reduced pressure. Water was added to the residue and the mixture was extracted with ether. The ether layer was washed with water and dried (MgSO₄). The solvent was distilled off, and the oily residue was subjected to silica gel (200 g) column chromatography. From the ether-hexane (3:2, v/v) eluate fractions, methyl 2-chloro-3-[4-(t-4-hydroxy-1-methyl-r-1-cyclohexylmethoxy)phenyl]propionate was obtained as an oil (8.0 g, 65.6%).

IR $\nu_{max}^{Neat}$cm$^{-1}$: 3350, 1740

NMR δ ppm in CDCl₃: 1.05(3H, s), 1.3 2.0(8H, m), 2.32(1H, s), 2.8

REFERENCE EXAMPLE 15

By a similar manner to Reference Example 14, the following compounds were synthetized.

Methyl 2-chloro-3-[4-(1-methyl-4-oxocyclohexylmethoxy)-phenyl]propionate

Yield: 58.7%

IR $\nu_{max}^{Neat}$cm$^{-1}$: 1740, 1705

NMR δ ppm in CDCl₃: 1.21(3H, s), 1.6–2.1(4H, m), 2.1–2.6(4H, m), 3.06(1H, q, J=14 and 7), 3.38(1H, q, J=14 and 7), 3.74(3H, s), 3.80(2H, s), 4.46(1H, t, J=7), 6.90(2H, d, J=9), 7.21(2H, d, J=9)

Methyl 2-chloro-3-[4-(1-methyl-3-oxocyclohexylmethoxy)-phenyl]propionate

Yield: 70.3%

IR $\nu_{max}^{Neat}$cm$^{-1}$: 1745, 1705

NMR δ ppm in CDCl₃: 1.04(3H, s), 1.5–2.6(8H, m), 3.04(1H, q, J=14 and 7), 3.34(1H, q, J=14 and 7), 3.66(2H, s), 3.71(3H, s), 4.40(1H, t, J=7), 6.82(2H, d, J=9), 7.18(2H, d, J=9)

Methyl 2-chloro-3-[4-(1-methyl-2-oxocyclohexylmethoxy)-phenyl]propionate

Yield: 57.5%

IR $\nu_{max}^{Neat}$cm$^{-1}$: 1740, 1705

NMR δ ppm in CDCl₃: 1.23(3H, s), 1.85(6H, broad), 2.45(2H, broad), 3.07(1H, q, J=14 and 7), 3.37(1H, q, J=14 and 7), 3.73(3H, s), 3.99(2H, s), 4.43(1H, t, J=7), 6.90(2H, d, J=9), 7.19(2H, d, J=9)

Methyl 2-chloro-3-[4-(c-4-hydroxy-1-methyl-r-1-cyclohexylmethoxy)phenyl]propionate Yield: 84.6%

IR $\nu_{max}^{Neat}$cm$^{-1}$: 3370, 1740

NMR δ ppm in CDCl₃: 1.0(3H, s), 1.2–2.0(8H, m), 2.57(1H, s), 3.07(1H, q, J=14 and 7), 3.37(1H, q, J=14 and 7), 3.73(3H, s), 3.75(2H, s), 4.43(1H, t, J=7), 6.88(2H, d, J=9), 7.18(2H, d, J=9)

Methyl 2-chloro-3-[4-(c-3-hydroxy-1-methyl-r-1-cyclohexylmethoxy)phenyl]propionate Yield: 52.8%

IR $\nu_{max}^{Neat}$cm$^{-1}$: 3370, 1740

NMR δ ppm in CDCl₃: 1.02(3H, s), 1.1-2.1(8H, m), 3.05(1H, q, J=14 and 7), 3.30(1H, q, J=14 and 7), 3.58(2H, s), 3.72(3H, s), 3.6-4.0(1H, m), 4.37(1H, t, J=7), 6.81(2H, d, J=9), 7.11(2H, d, J=9)

Methyl 2-chloro-3-[4-(t-3-hydroxy-1-methyl-r-1-cyclohexylmethoxy)phenyl]propionate Yield: 52.6%

IR $\nu_{max}^{Neat}$ cm⁻¹: 3370, 1740

NMR δ ppm in CDCl₃: 1.06(3H, s), 1.1-2.1(8H, m), 3.05(1H, q, J=14 and 7), 3.29(1H, q, J=14 and 7), 3.5-3.9(1H, m) 3.66(2H, s), 3.71(3H, s), 4.37(1H, t, J=7), 6.80(2H, d, J=9), 7.10(2H, d, J=9)

Methyl 2-chloro-3-[4-(4-oxocyclohexylmethoxy)phenyl]propionate

Yield: 35.1% m.p.: 71°-72° C. (Recrystallization from methanol)

REFERENCE EXAMPLE 16

4-(t-3-hydroxy-1-methyl-r-1-cyclohexylmethoxy)nitrobenzene (146 g) was disolved in methanol (1 l), and 10% paradium-carbon (50% wet, 10 g) was added. The catalytic reduction was carried out at room temperature and 1 atmosphere. After absorption of hydrogen completed, the catalyst was filtered off and the filtrate was concentrated under reduced pressure. The resulting oil was dissolved in acetone (1.5 l) and cooled to 0° C. 48% Aqueous solution (284 g) of hydrogen bromide was added and then sodium nitrate (41.4 g) in water (100 ml) was added dropwise to the mixture at 5° C. or below. After stirring at 5° C. for 15 minutes, methyl acrylate (281 g) was added and the mixture was warmed to 35° C. Cuprous oxide powder (1.0 g) was added portionwise with vigorous stirring, whereupon violent nitrogen gas evolution occurred with evolution of heat. Stirring was continued until the mixture returned to room temperature. The mixture was concentrated under reduced pressure. Water was added to the residue and the mixture was extracted with ether. The ether layer was washed with water and dried (MgSO₄). The solvent was distilled off, whereby oily substance (204 g, 96.2%) of methyl 2-bromo-3-[4-(t-3-hydroxy-1-methyl-r-1-cyclohexylmethoxy)phenyl]propionate was obtained. The oil was subjected to column chromatography using silica gel. Elution with cyclohexane-ethyl acetate (3:1. v/v) gave an oil.

IR $\nu_{max}^{Neat}$ cm⁻¹: 3350, 1740

NMR δ ppm in CDCl₃: 1.07(3H, s), 1.3-2.2(8H, m), 3.11(1H, q, J=14 and 17), 3.38(1H, q, J=14 and 7), 3.66(2H, s), 3.70(3H, s), 3.8(1H, m), 4.34(1H, t, J=7), 6.79(2H, d, J=9), 7.09(1H, d, J=9)

EXAMPLE 1

To a solution of 2-chloro-3-[4-(c-4-hydroxy-1-methyl-r-1-cyclohexylmethoxy)phenyl]propionic acid (11.0 g) in sulfolane (100 ml), thiourea (3.7 g) was added, and the mixture was stirred at 120° C. for 3 hours. Then, 2N HCl (100 ml) was added and heating was continued under reflux for 8 hours. After cooling, water was added and the mixture was extracted with ether. The ether layer was washed with water and dried (MgSO₄). The ether was distilled off to leave crystalline 5-[4-(c-4-hydroxy-1-methyl-r-1-cyclohexylmethoxy)benzyl]-thiazolidine-2,4-dione (6.9 g, 60.5%), which was recrystallized from ethyl acetate-hexane. m.p. 120°-121° C.

EXAMPLE 2

To a suspension of 5-[4-(1-methyl-2-oxocyclohexylmethoxy)benzyl]thiazolidine-2,4-dione (5.2 g) in methanol (50 ml), sodium borohydride (0.757 g) was added under ice cooling. The mixture was stirred with ice cooling for 30 minutes, then acetic acid (2 ml) was added. The mixture was poured into water and extracted with benzene. The extract was washed with water and dried (MgSO₄). The benzene was distilled off, and the oily residue was subjected to silica gel (100 g) column chromatography. From the benzene-acetone (10:1, v/v) eluate fractions, 5-[4-(2-hydroxy-1-methylcyclohexylmethoxy)benzyl]thiazolidine-2,4-dione was obtained as a powder (4.2 g, 80.8%). m.p. 101°-103° C. The thus-obtained powder was a mixture of two isomers different in the configuration of the hydroxyl group on the cyclohexane ring.

Calculated for C₁₈H₂₃NO₄S: C, 61.87; H, 6.63; N, 4.01; Found: C, 62.02; H, 6.34; N, 4.20.

EXAMPLE 3

To a solution of 5-[4-(t-4-hydroxy-1-methyl-r-1-cyclohexylmethoxy)benzyl]thiazolidine-2,4-dione (1.5 g) in acetone (30 ml), Jones' reagent (5 ml) was added dropwise with ice cooling. The mixture was stirred with ice cooling for 30 minutes and methanol (5 ml) was added thereto. The solvent was distilled off under reduced pressure. Water was added to the residue, and the mixture was extracted with ethyl acetate. The organic layer was washed with water and dried (MgSO₄), and the solvent was distilled off to give 5-[4-(1-methyl-4-oxocyclohexylmethoxy)benzyl]thiazolidine-2,4-dione as crystals (1.2 g, 80.0%), which was recrystallized from ethyl acetate-hexane. m.p. 134°-135° C.

EXAMPLE 4

By a similar manner to Example 1, 2 or 3, the following compounds were prepared.

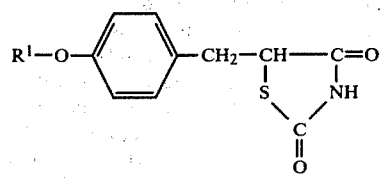

| R¹ | m.p. (°C.) | recrystallization solvent | Yield (%) | Analogous Example |
|---|---|---|---|---|
| ![CH3/CH2- with O=] | 134-135 | ethyl acetate-hexane | 73.9 | 1 |
| ![CH3/CH2- with O=] | 100-102* | ethyl acetate-hexane | 74.0 / 85.5 | 1 / 3 |
| ![CH3/CH2- with O=] | 123-125* | ethyl acetate-hexane | 77.9 | 1 |
| ![CH3/CH2- with HO] | 171-172 | ethyl acetate-hexane | 58.5 / 18.1 | 1 / 2 |

-continued

R¹—O—⟨phenyl⟩—CH₂—CH—C=O
                    |    |
                    S    NH
                     \  /
                      C
                      ||
                      O

| R¹ | m.p. (°C.) | recrystallization solvent | Yield (%) | Analogous Example |
|---|---|---|---|---|
| HO⫻⟨cyclohexyl⟩(CH₃)(CH₂—) | 120–121 | ethyl acetate-hexane | 12.3 | 2 |
| HO⟨cyclohexyl⟩(CH₃)(CH₂—) | 124–125* | ethyl acetate-hexane | 42.6 | 1 |
| HO⟨cyclohexyl⟩(CH₃)(CH₂—) | 130–131* | ethyl acetate-hexane | 46.0 | 1 |
| O=⟨cyclohexyl⟩—CH₂— | 176–177 | ethanol | 79.7 | 1 |

Melting point with asteric (*) is that of a mixture of two diastereomers.

EXAMPLE 5

To a solution of methyl 2-bromo-3-[4-(t-3-hydroxy-1-methyl-r-1-cyclohexylmethoxy)phenyl]propionate (200 g) in ethanol (1.5 l), thiourea (39.5 g) and sodium acetate (42.7 g) were added. The mixture was refluxed for 3 hours and the reaction mixture was concentrated under reduced pressure. Water was added and the mixture was extracted with ethyl acetate. The ethyl acetate layer was washed with water and dried (MgSO₄), and the solvent was distilled off to leave crystalline 5-[4-(t-3-hydroxy-1-methyl-r-1-cyclohexylmethoxy)benzyl]-2-iminothiazolidin-4-one (110 g, 59.1%), which was recrystallized from ethyl acetate. m.p. 219°–220° C.

EXAMPLE 6

A mixture of 5-[4-(t-3-hydroxy-1-methyl-r-1-cyclohexylmethoxy)benzyl]-2-iminothiazolidin-4-one (35.0 g), 2N HCl (200 ml) and 2-methoxyethanol (200 ml) was refluxed for 6 hours. Water was added and the mixture was extracted with ethyl acetate. The ethyl acetate layer was washed with water and dried (MgSO₄), and the solvent was distilled off. The residue was subjected to column chromatography using silica gel. Elution with benzene-acetone (10:1, v/v) gave crystals of 5-[4-(t-3-hydroxy-1-methyl-r-1-cyclohexylmethoxy)benzyl]thioazolidine-2,4-dione (33.0 g, 94.3%). They were recrystallized from ethyl acetate-hexane. m.p. 124°–125° C.

What is claimed is:

1. A compound of the general formula

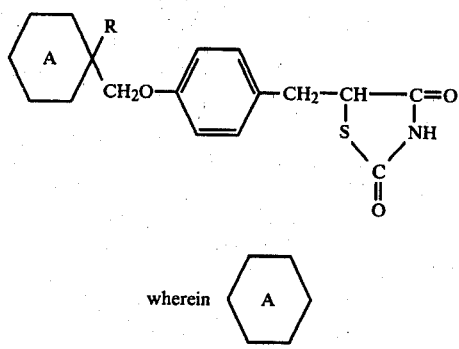

wherein A is a cyclohexane ring having an oxo or hydroxyl group as a substituent on any of the methylene groups constituting the ring and R is a hydrogen atom or a lower alkyl group having 1 to 4 carbon atoms.

2. A compound as claimed in claim 1, wherein R is methyl.

3. A compound as claimed in claim 1, wherein

is a cyclohexane ring having an oxo group as a substituent on any of the methylene groups constituting the ring.

4. A compound as claimed in claim 1, wherein

is a cyclohexane ring having a hydroxyl group as a substituent on any of the methylene groups constituting the ring.

5. A compound as claimed in claim 1, wherein the compound is 5-[4-(3-hydroxy-1-methyl-1-cyclohexylmethoxy)benzyl]thiazolidine-2,4-dione.

6. A compound as claimed in claim 1, wherein the compound is 5-[4-(4-hydroxy-1-methyl-1-cyclohexylmethoxy)benzyl]thiazolidine-2,4-dione.

7. A compound as claimed in claim 1, wherein the compound is 5-[4-(t-3-hydroxy-1-methyl-r-1-cyclohexylmethoxy)benzyl]thiazolidine-2,4-dione.

8. A compound as claimed in claim 1, wherein the compound is 5-[4-(t-4-hydroxy-1-methyl-r-1-cyclohexylmethoxy)benzyl]thiazolidine-2,4-dione.

9. A compound as claimed in claim 1, wherein the compound is 5-[4-(c-4-hydroxy-1-methyl-r-1-cyclohexylmethoxy)benzyl]thiazolidine-2,4-dione.

* * * * *